(12) United States Patent
Martens

(10) Patent No.: US 9,119,543 B2
(45) Date of Patent: Sep. 1, 2015

(54) SYSTEM AND METHOD FOR DEEP BRAIN STIMULATION

(75) Inventor: Hubert Cécile François Martens, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 80 days.

(21) Appl. No.: 13/321,190

(22) PCT Filed: Jul. 23, 2010

(86) PCT No.: PCT/IB2010/053352
§ 371 (c)(1),
(2), (4) Date: Nov. 18, 2011

(87) PCT Pub. No.: WO2011/013041
PCT Pub. Date: Feb. 3, 2011

(65) Prior Publication Data
US 2012/0150256 A1 Jun. 14, 2012

(30) Foreign Application Priority Data
Jul. 30, 2009 (EP) .................................... 09166840

(51) Int. Cl.
*A61B 5/04* (2006.01)
*A61N 1/36* (2006.01)
*A61B 5/00* (2006.01)
*A61N 1/05* (2006.01)

(52) U.S. Cl.
CPC ........ *A61B 5/04004* (2013.01); *A61N 1/36182* (2013.01); *A61B 5/04001* (2013.01);
(Continued)

(58) Field of Classification Search
CPC ........... A62N 1/36182; A62N 1/36128; A62N 1/3605; A62N 1/36025; A62N 1/36082; A62N 1/36014; A62N 1/36; A61B 5/04004; A61B 5/04001

USPC ............. 607/45, 139, 148; 600/544–545, 393
See application file for complete search history.

(56) References Cited

U.S. PATENT DOCUMENTS 6,016,449 A * 1/2000 Fischell et al. .................. 607/45
6,366,813 B1 4/2002 DiLorenzo
(Continued)

FOREIGN PATENT DOCUMENTS

CN 1597011 A 3/2005

OTHER PUBLICATIONS

International Search Report and Written Opinion for International Patent Application No. PCT/IB2010/053352 dated Nov. 5, 2010.
(Continued)

*Primary Examiner* — Catherine Voorhees
(74) *Attorney, Agent, or Firm* — Shumaker & Sieffert, P.A.

(57) ABSTRACT

A system (10) and a method for deep brain stimulation are provided. The system (10) comprises a probe (11) and a processor (14). The probe (11) comprises an array of sensing electrodes (12) for acquiring signals representing neuronal activity at corresponding positions in a brain and an array of stimulation electrodes (12) for applying stimulation amplitudes to corresponding brain regions. The processor (14) is operably coupled to the sensing electrodes (12) and the stimulation electrodes (12) and is arranged for performing the method according to the invention. The method comprises receiving (21) the acquired signals from the sensing electrodes (12), processing (22) the acquired signals to find at least one brain region with atypical neuronal activity, based on the acquired signals determining (23) a spatial distribution of stimulation amplitudes over the array of stimulation electrodes (12), and applying (24) the spatial distribution of stimulation amplitudes to the array of stimulation electrodes (12) in order to stimulate the at least one region with atypical neuronal activity.

53 Claims, 4 Drawing Sheets

(52) U.S. Cl.
CPC ....... *A61B5/7239* (2013.01); *A61B 2562/0209* (2013.01); *A61B 2562/046* (2013.01); *A61N 1/0534* (2013.01)

(56) References Cited

U.S. PATENT DOCUMENTS

| | | |
|---|---|---|
| 2002/0169485 A1* | 11/2002 | Pless et al. .................. 607/48 |
| 2004/0111127 A1 | 6/2004 | Gliner |
| 2004/0181263 A1 | 9/2004 | Balzer et al. |
| 2006/0173510 A1 | 8/2006 | Besio et al. |
| 2008/0114417 A1* | 5/2008 | Leyde ........................ 607/60 |

OTHER PUBLICATIONS

Official Action issued by Israeli Patent Office on Jan. 7, 2014 in connection with Israeli Patent Application No. 217735.

Second Office Action dated Jun. 30, 2014 for Chinese Patent Application No. 201080033903.

* cited by examiner

SYSTEM AND METHOD FOR DEEP BRAIN STIMULATION

CROSS-REFERENCE TO RELATED APPLICATIONS

This application is a National Stage Patent Application of International Application No. PCT/IB2010/053352, filed Jul. 23, 2010, which claims priority to European Patent Application No. 09166840.0 filed on Jul. 30, 2009, each of which are incorporated herein by reference in their entirety.

FIELD OF THE INVENTION

This invention relates to a system for deep brain stimulation, the system comprising a probe with an array of stimulation electrodes for applying stimulation amplitudes to corresponding brain regions, a processor for determining a spatial distribution of stimulation amplitudes over the array of stimulation electrodes, and for applying the determined spatial distribution of stimulation amplitudes to the array of stimulation electrodes in order to stimulate the at least one region with atypical neuronal activity.

This invention further relates to a method for determining a spatial distribution of stimulation amplitudes for deep brain stimulation and a computer program product for performing said method.

BACKGROUND OF THE INVENTION

Deep brain stimulation (DBS) is a technique in which mild electrical pulses are applied to brain tissue to disrupt pathological activity. Existing DBS devices have four large (typically 6 mm$^2$), cylindrically shaped, electrodes to deliver the pulses to the tissue. This results in a very non-specific delivery of the electrical energy to the tissue. The DBS targets can be as small as 1 mm or less and the stimulation currents cannot be accurately targeted to such small features with these existing DBS devices. This non-specific delivery has several drawbacks. It may, for example, lead to induction of side-effects due to current exciting tissues adjacent to target areas. Additionally, it may result in sub-optimal therapeutic effects due to current not optimally covering the target structures. New DBS devices under development may address this issue by providing large numbers of electrodes (e.g. 16-128) distributed along the probe in an array-like fashion (axially and azimuthally). By having such a high-density array of stimulation electrodes in principle very accurate delivery of electrical stimuli is possible, improving the mentioned shortcomings of the larger electrodes.

With so many stimulation electrodes it is important to distribute the electrical stimuli optimally. The optimization problem for finding the best distribution of stimuli over the array is highly complex due to the enormous degrees of freedom offered by the new high-resolution DBS devices. Therefore, there is a need for a practical and reliable method to quickly determine the optimum settings. Model-based optimization approaches are being developed for this purpose. However, these approaches suffer from intrinsic limitations since not all parameters are and can be known in sufficient detail (most notably the local inhomogeneous and anisotropic conductivity distributions strongly influence the field but are very hard to accurately measure). Hence inaccuracy remains with these approaches.

OBJECT OF THE INVENTION

It is an object of the invention to provide a less complex and more reliable method and system for determining a spatial distribution of the stimulation amplitudes.

SUMMARY OF THE INVENTION

According to a first aspect of the invention, this object is achieved by providing a system for deep brain stimulation, the system comprising a probe and a processor. The probe comprises an array of sensing electrodes for acquiring signals representing neuronal activity at corresponding positions in a brain and an array of stimulation electrodes for applying stimulation amplitudes to corresponding brain regions. The processor is operably coupled to the sensing electrodes and the stimulation electrodes. The processor is arranged for receiving the acquired signals from the sensing electrodes, processing the acquired signals to find at least one brain region with atypical neuronal activity, based on the acquired signals determining a spatial distribution of stimulation amplitudes over the array of stimulation electrodes, and applying the spatial distribution of stimulation amplitudes to the array of stimulation electrodes in order to stimulate the at least one region with atypical neuronal activity.

The array of sensing electrodes is used for determining a spatial overview of the neuronal activity. From the measured neuronal activity it is determined whether and where there are pathologically behaving neurons or neuronal structures in the brain region of interest. When the local hotspots of pathological activity are located, the processor determines a spatial distribution of stimulation amplitudes in order to target those hotspots.

In an embodiment of the system according to the invention, the neuronal activity in a region in the brain is considered atypical when the acquired signal exceeds a predetermined level. In more advanced embodiments, more complex processing is used for finding the sources of pathological electrical activity. The processing may, for example, comprise band pass filtering the acquired signals. For example, an increased beta-band activity (8-30 Hz) may relate to possible symptoms of Parkinson's disease.

The processing may comprise computing a second spatial derivative of the acquired signals or of specific features extracted from the acquired signals. The second spatial derivative of the acquired signal provides a clear indication of the activity sources and thus provides useful information for determining a suitable special distribution of the stimulation amplitudes to apply. The spatial distribution of stimulation amplitudes may be chosen to be proportional to the second spatial derivative of the acquired signals.

At least one of the sensing electrodes and at least one of the stimulation electrodes are preferably combined in one combined electrode. Switching means may be provided for switching between the sensing and stimulating function of the combined electrodes. The switching may be done for all combined electrodes simultaneously or for each combined electrode individually.

According to a second aspect of the invention, a method is provided for determining a spatial distribution of stimulation amplitudes. The method comprises receiving from an array of sensing electrodes on a sensing probe, acquired signals representing neuronal activity at corresponding positions in a brain, processing the acquired signals to find at least one brain region with atypical neuronal activity, and based on the acquired signals determining a distribution of stimulation amplitudes over the array of the stimulation electrodes.

These and other aspects of the invention are apparent from and will be elucidated with reference to the embodiments described hereinafter.

DETAILED DESCRIPTION OF THE INVENTION

Figure 1:
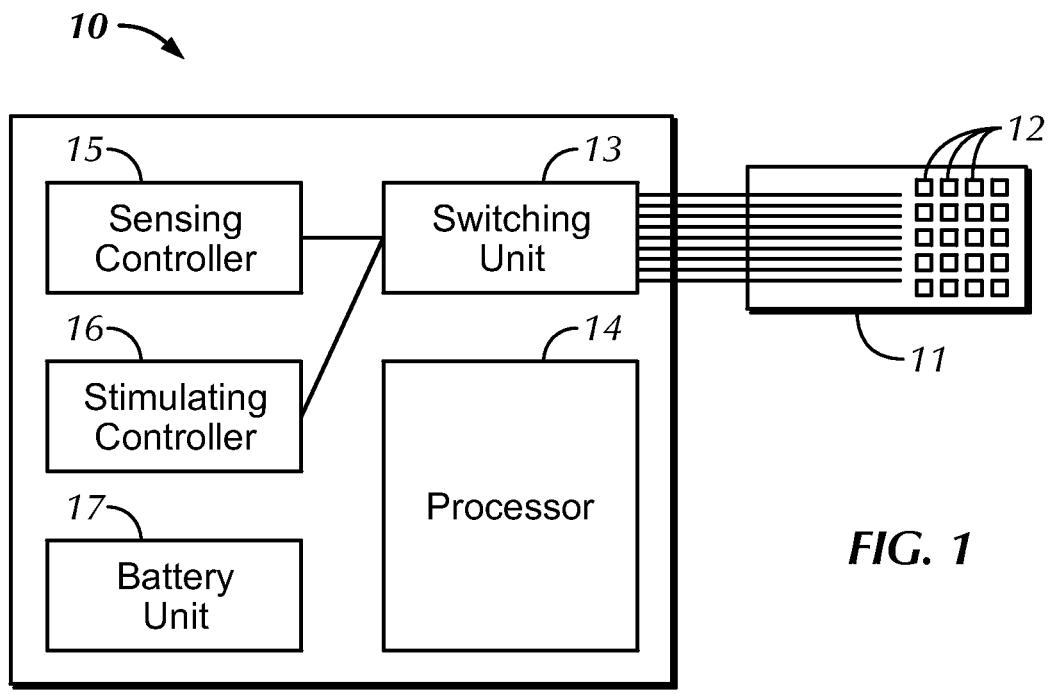
FIG. 1 schematically shows a system for deep brain stimulation according to the invention.

FIG. 1 schematically shows a system 10 for deep brain stimulation according to the invention. The system 10 comprises a probe 11 with an array of electrodes 12. The electrodes 12 are preferably regularly arranged on a portion of the probe surface. Selected electrodes 12 may be designed for sensing, other electrodes may be provided for stimulating. The dimensions of sensing electrodes 12 may differ from the dimensions of the stimulating electrodes 12. For accurate measurements, the electrodes 12 are preferably small. For lower impedance for the stimulus delivery, the stimulating electrodes 12 are preferably somewhat larger.

In a preferred embodiment of the system 10 according to the invention, all electrodes 12 can be used for sensing as well as for stimulating. Switching unit 13 is provided for switching between the sensing and the stimulating function of the electrodes 12. The dimensions of the electrodes 12 are preferably balanced such as to allow both accurate sensing and low impedance for the stimulating. The target sizes, e.g. sub-parts of the subthalamic nucleus, may be as small as 1 mm. For enabling accurate sensing, the dual purpose electrodes preferably therefore have a surface area in the range of 0.1-1 mm$^2$.

An important advantage of the use of dual purpose electrodes 12 is that the electrical problem of determining the suitable distribution of stimulation amplitudes becomes symmetric and thus gives the best results. The switching unit 13 is controlled by a processor 14. The processor 14 may control the switching unit 13 to put all electrodes 12 in the same mode (sensing or stimulating) or may select to use part of the electrodes 12 for stimulating while other electrodes 12 are in the sensing mode.

Under influence of the processor 14, the switching unit 13 either couples the electrodes 12 to a sensing controller 15 or to a stimulating controller 16. The system 10 is powered by a battery unit 17 which may comprise a power management module. The battery unit 17 powers all parts of the system requiring electrical power. The processor 14 controls the functioning of the system 10 and is operative to instruct the above mentioned functional parts of the system 10 to determine and to apply a spatial distribution of stimulation amplitudes for deep brain stimulation to the electrodes 12.

It is to be noted that the invention may also be used in an off-line system, which receives the sensed signals from an implanted probe of a separate measurement system. The off-line system then processes the signals in accordance with the current invention and sends a spatial distribution of stimulation signals to the implanted probe. The implanted probe provides the stimuli according to the received spatial distribution of stimulation signals.

Figure 2:
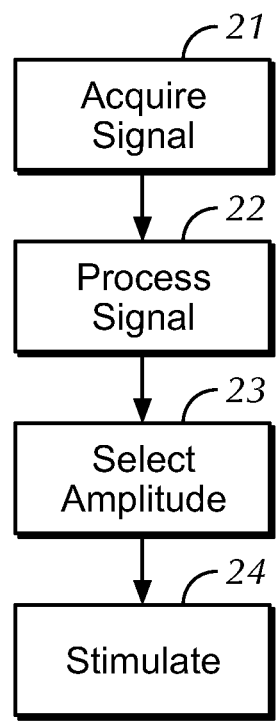
FIG. 2 shows a flow diagram of a method according to the invention.

FIG. 2 shows a flow diagram of a method according to the invention. The method may be executed by the system 10 of FIG. 1, under control of the processor 14. The method starts with a sensing step 21 for acquiring signals representing neuronal activity from the electrodes 12 on the probe 11. For this purpose the processor 14 instructs the switching unit 13 to couple at least part of the electrodes 12 to the sensing controller 15. The electrodes 12 pick up signals representing the neuronal activity at (or close to) the electrodes. The processor 14 then receives the acquired signals via the sensing controller 15. An example of a sensing signal that may be received from the electrodes 12 is provided in FIG. 3.

Figure 3:
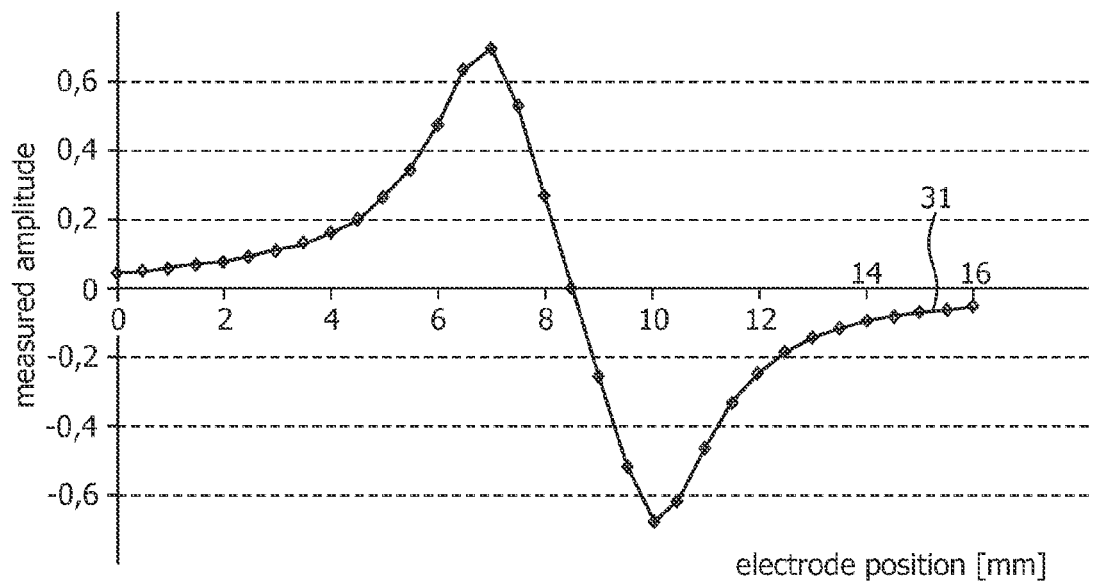
FIG. 3 shows an example of a signal acquired by an array of sensing electrodes.

FIG. 3 shows an example of a signal 31 acquired by an array of sensing electrodes 12. The signal 31 shown in FIG. 3 is a simulated signal 31 given for explanatory purposes. In the simulated situation resulting in this measured neuronal activity signal 31, a 1-dimensional probe 11 is used having 33 equally spaced electrodes 12 with 0.5 mm distance. The height of the electrode array runs from 0 to 16 mm. A source/sink of pathological (electrical) neuronal activity is positioned 1 mm laterally from the probe 11 at heights 7 and 10 mm respectively, resulting in peak amplitudes measured at the corresponding electrodes 12.

After measuring the neuronal activity in the brain, the processor 14 processes the acquired signals 31 in signal processing step 22 (FIG. 2) in order to find one or more brain regions with atypical neuronal activity. Such regions with atypical neuronal activity may indicate pathologically behaving neurons which may benefit from electrical stimulation. In the signal processing step 22, many different algorithms may be used for recognizing atypical or suspect neuronal activity. In a very basic algorithm, the processor 14 may look for signal amplitudes exceeding a predetermined (positive or negative) trigger level. The stimulation amplitude may then be directed at the electrodes 12 measuring the excessive neuronal activity.

In more advanced algorithms, features may be extracted from the acquired signal 31. For example, a band pass filter may be used for detecting neuronal activity in a specific frequency range. An increased activity in the beta-band (8-30 Hz) may, for example, relate to symptoms of Parkinson's disease. This may be treated by stimulating the electrodes 12 having the highest amplitude of processed signal. In the beta-band example, the electrodes 12 picking up the most signal in the 8-30 Hz frequency range may be stimulated.

A preferred algorithm for searching for atypically acting neuronal tissue is demonstrated below with reference to FIG. 4 to 6. This preferred algorithm makes use of a technique known as current-source-density imaging combined with the Helmholtz reciprocity theorem.

Figure 4:
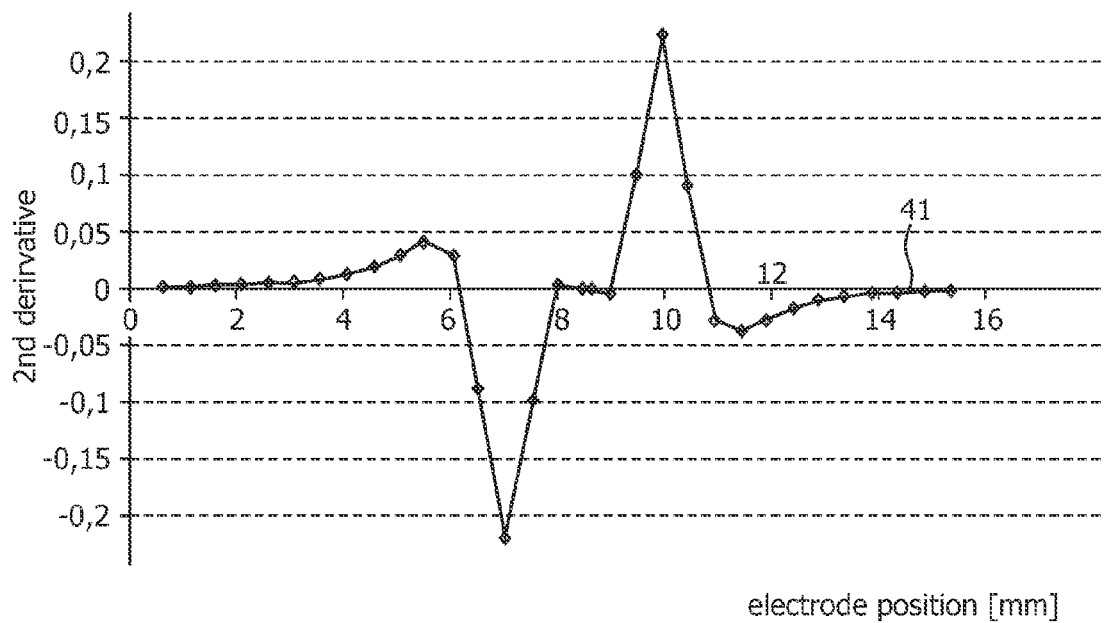
FIG. 4 shows the second spatial derivative of the signal of FIG. 2.

FIG. 4 shows the second spatial derivative 41 of the signal 31 of FIG. 3. The computed second spatial derivative provides a very clear indication of the spatial location of a neuronal activity source, also when such a source is less visible from the acquired signal 31 directly. Alternatively, the system may use the second spatial derivative of a band-passed filtered signal or of other features extracted from the measured signal.

In amplitude selecting step 23 (FIG. 2), a suitable spatial distribution of stimulation amplitudes is determined. This spatial distribution may be derived directly from the acquired signal 31 or indirectly via additional processing steps.

According to the Helmholtz reciprocity theorem, application of a current distribution to the electrode 12 array in direct relation to the computed second spatial derivative values leads to the electrical stimulation being directed towards the source of the measured activity.

Figure 5:
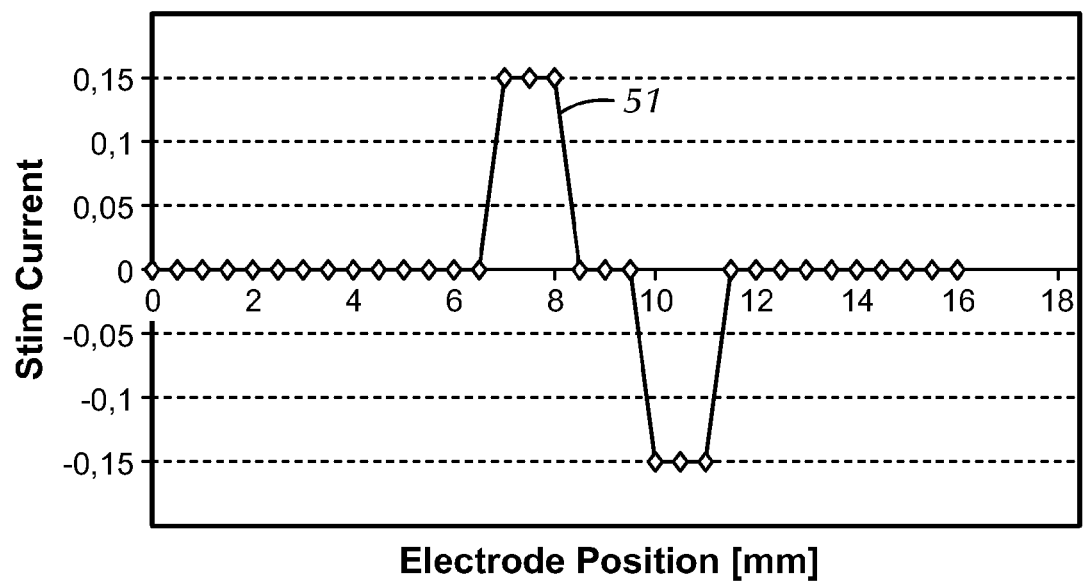
FIG. 5 shows an exemplary spatial distribution of stimulation amplitudes.

FIG. 5 shows an exemplary spatial distribution of stimulation amplitudes 51 as determined based on the second spatial derivative values 41 shown in FIG. 4. For this distribution 51 only two independent pulse generators are assumed to be available. First the two regions of second spatial derivative values most strongly deviating from zero are determined: 6.5-7.5 mm and 9.5-10.5 mm. In both areas three electrodes are available. Averaging and scaling over both regions, a stimulation amplitude +0.15 is applied to the first region of three electrodes and −0.15 to the second region of three electrodes. The determining of the spatial distribution of stimulation amplitudes 51 is performed by the processor 14.

In stimulating step 24, the processor 14 then instructs the stimulation controller 16 to apply the spatial distribution of stimulation amplitudes 51 to the electrodes 12, while the switching unit 13 puts the probe, or at least the necessary electrodes 12, in a stimulus mode.

Figure 6:
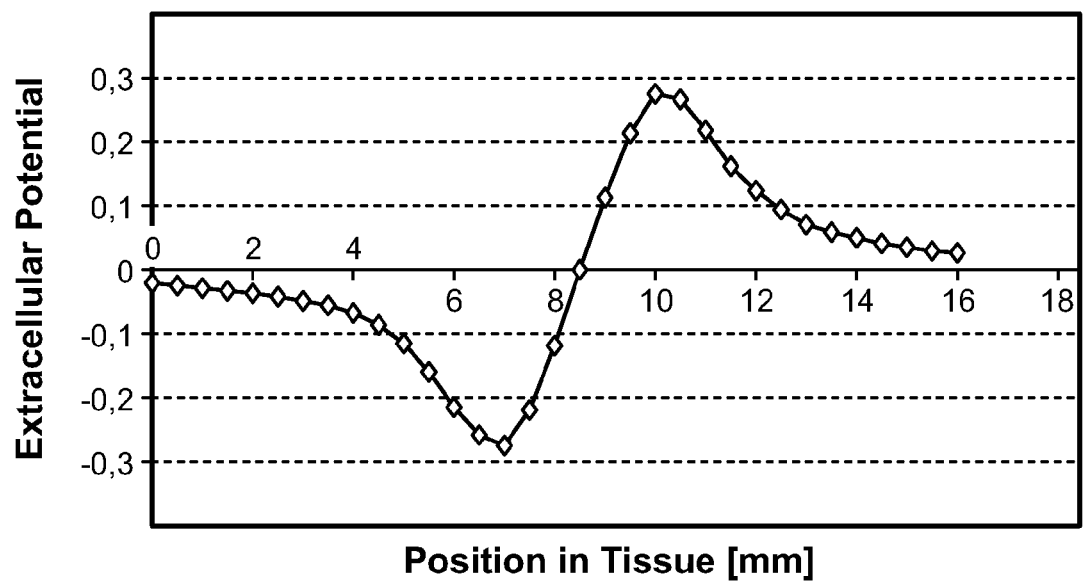
FIG. 6 shows the extra-cellular electrical potential distribution resulting from the stimulation amplitudes of FIG. 4.

FIG. 6 shows a stimulation field potential according to the method of the invention; it was derived from the second derivative for neuronal activity (FIG. 4) positioned 1 mm lateral and at heights 7 mm and 10 mm. This plot shows that strong potential gradients result at the location of the presumed neuronal activity.

Figure 7:
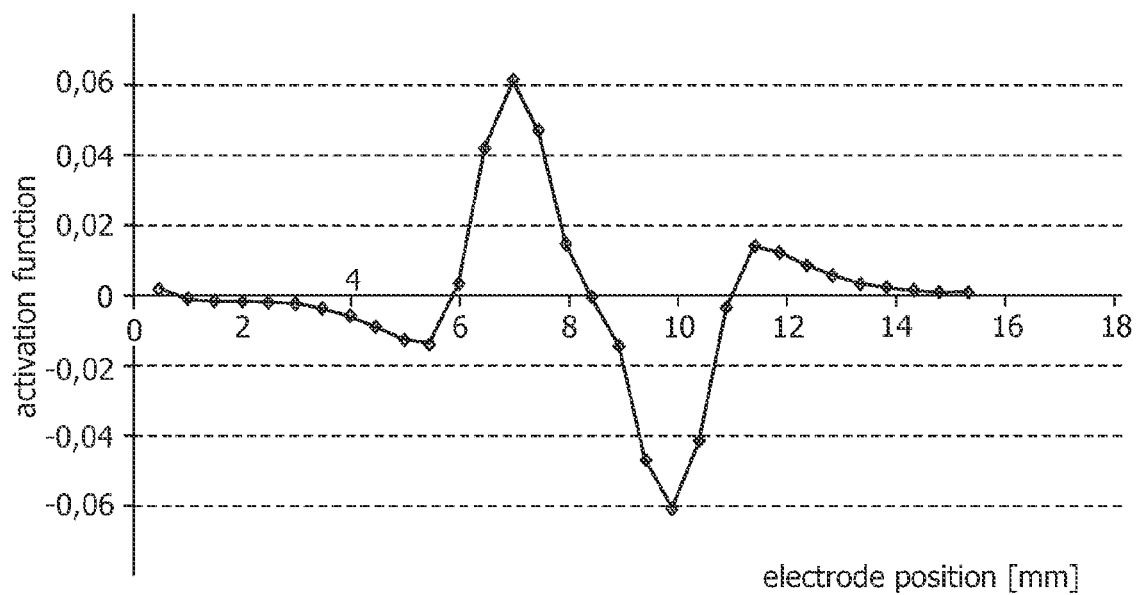
FIG. 7 shows the activating function for the targeted neuronal tissue.

FIG. 7 shows that the so-called activation function (which drives the neuronal activation) and which is proportional to $2^{nd}$ derivative of the applied stimulus field peaks at the desired locations of 7 and 10 mm.

In an embodiment of the method according to the invention, neuronal activity is measured at the electrodes 12 twice. Once without the patient on medication and once with the patient off medication. Those electrodes 12 where the largest differences in activity (or derived features) are measured are used for providing the stimulation amplitudes. As a result the drug-response provides a pre-filtering on which electrodes to use.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for deep brain stimulation, the system comprising:

a probe with an array of sensing electrodes and an array of stimulation electrodes, wherein the array of sensing electrodes and the array of stimulation electrodes are arranged on a common surface of the probe, wherein the probe is configured to be implanted into brain tissue, wherein the array of sensing electrodes is configured to acquire signals representing neuronal activity at corresponding positions in a brain, and wherein the array of stimulation electrodes is configured to apply stimulation amplitudes to corresponding brain regions; and a processor, operably coupled to the array of sensing electrodes and the array of stimulation electrodes, configured to:

receive the acquired signals from the array of sensing electrodes, process the acquired signals to generate a second spatial derivative corresponding to the array of sensing electrodes, find an indication of at least one brain region with atypical neuronal activity, responsive to finding the indication, determine a spatial distribution of stimulation amplitudes over the array of stimulation electrodes based on the second spatial derivative, and apply the spatial distribution of stimulation amplitudes to the array of stimulation electrodes in order to stimulate the at least one brain region with atypical neuronal activity.

2. A system for deep brain stimulation as claimed in claim 1, wherein at least one of the sensing electrodes and at least one of the stimulation electrodes are combined in one combined electrode.

3. A system for deep brain stimulation as claimed in claim 2, wherein the one combined electrode has an electrode surface with a surface area in the range of 0.1- 1 mm$^2$.

4. A system for deep brain stimulation as claimed in claim 1, wherein the indication of the neuronal activity in the at least one brain region is considered atypical when the acquired signals exceeds a predetermined level.

5. A system for deep brain stimulation as claimed in claim 1, wherein the indication of the neuronal activity in the at least one brain region is considered atypical when the second spatial derivative exceeds a predetermined limit.

6. A system for deep brain stimulation as claimed in claim 1, wherein the spatial distribution of stimulation amplitudes is substantially proportional to the second spatial derivative.

7. A system for deep brain stimulation as claimed in claim 1, wherein, to process the acquired signals, the processor is configured to band pass filter the acquired signals to generate the second spatial derivative.

8. A system for deep brain stimulation as claimed in claim 7, wherein the indication of the neuronal activity in the at least one brain region is considered atypical when the band-passed signal shows excessive activity.

9. A system for deep brain stimulation as claimed in claim 1, wherein, to process the acquired signals, the processor is configured to extract at least one specific feature from the acquired signals to generate the second spatial derivative.

10. A system for deep brain stimulation as claimed in claim 9, wherein the processor is configured to process the acquired signals to generate the second spatial derivative based on the extracted specific feature.

11. A system for deep brain stimulation as claimed in claim 1, wherein the processor is configured to determine the spatial distribution of stimulation amplitudes such that the stimulation current distributed to each of the stimulation electrodes is determined based on values of the second spatial derivative of the acquired signals received from corresponding sensing electrodes.

12. A system for deep brain stimulation as claimed in claim 11, wherein the corresponding sensing electrodes are adjacent to the respective stimulation electrodes.

13. A system for deep brain stimulation as claimed in claim 11, wherein at least some of the corresponding sensing electrodes are the same as and combined with the respective stimulation electrodes.

14. A system for deep brain stimulation as claimed in claim 1, wherein the processor is configured to determine the spatial distribution of stimulation amplitudes such that the stimulation current distributed to each of the stimulation electrodes is at a largest level for stimulation electrodes that have corresponding sensing electrodes for which the second spatial derivative of the acquired signals received from the corresponding sensing electrodes has largest values.

15. A system for deep brain stimulation as claimed in claim 14, wherein the corresponding sensing electrodes are adjacent to the respective stimulation electrodes.

16. A system for deep brain stimulation as claimed in claim 14, wherein at least some of the corresponding sensing electrodes are the same as and combined with the respective stimulation electrodes.

17. A system for deep brain stimulation as claimed in claim 1, wherein the array of sensing electrodes includes a 1-dimensional array of sensing electrodes.

18. A system for deep brain stimulation as claimed in claim 17, wherein the second spatial derivative includes a second spatial derivative of the acquired signals received by the 1-dimensional array of sensing electrodes.

19. A system for deep brain stimulation as claimed in claim 17, wherein the sensing electrodes of the 1-dimensional array are equally spaced by a 0.5 millimeter distance.

20. A system for deep brain stimulation as claimed in claim 17, wherein the 1-dimensional array of sensing electrodes includes 33 sensing electrodes.

21. A system for deep brain stimulation as claimed in claim 17, wherein the 1-dimensional array of sensing electrodes comprises a length of 16 millimeters.

22. A system for deep brain stimulation as claimed in claim 1, wherein the array of stimulating electrodes includes a 1-dimensional array of stimulating electrodes.

23. A system for deep brain stimulation as claimed in claim 22, wherein the spatial distribution of stimulation amplitudes includes a spatial distribution of stimulation amplitudes applied to the 1-dimensional array of stimulating electrodes.

24. A system for deep brain stimulation as claimed in claim 22, wherein the stimulating electrodes of the 1-dimensional array are equally spaced by a 0.5 millimeter distance.

25. A system for deep brain stimulation as claimed in claim 22, wherein the 1-dimensional array of stimulating electrodes includes 33 sensing electrodes.

26. A system for deep brain stimulation as claimed in claim 22, wherein the 1-dimensional array of stimulating electrodes comprises a length of 16 millimeters.

27. A method for deep brain stimulation, the method comprising:
receiving, from an array of sensing electrodes on the probe implanted into brain tissue, acquired signals representing neuronal activity at corresponding positions in a brain, wherein the probe includes the array of sensing electrodes and an array of stimulation electrodes, wherein the array of sensing electrodes and the array of stimulation electrodes are arranged on a common surface of the probe, and wherein the array of stimulation electrodes is configured to apply stimulation amplitudes to corresponding brain regions;
processing the acquired signals to generate a second spatial derivative corresponding to the array of sensing electrodes;
finding an indication of at least one brain region with atypical neuronal activity; and
responsive to finding the indication, determining a distribution of stimulation amplitudes over the array the stimulation electrodes based on the second spatial derivative.

28. The method of claim 27, further comprising
applying the spatial distribution of stimulation amplitudes to the array of stimulation electrodes in order to stimulate the at least one brain region with atypical neuronal activity.

29. The method of claim 27, wherein processing the acquired signals to generate the second spatial derivative includes band pass filtering the acquired signals.

30. The method of claim 27, wherein processing the acquired signals to generate the second spatial derivative includes extracting at least one specific feature from the acquired signals.

31. The method of claim 27, wherein processing the acquired signals to generate the second spatial derivative further includes computing the second spatial derivative based on the extracted specific feature.

32. A non-transitory computer readable storage medium comprising instructions that cause a processor to;
receive, from an array of sensing electrodes on a probe implanted into brain tissue, acquired signals representing neuronal activity at corresponding positions in a brain, wherein the probe includes the array of sensing electrodes and an array of stimulation electrodes, wherein the array of sensing electrodes and the array of stimulation electrodes are arranged on a common surface of the probe, and wherein the array of stimulation electrodes is configured to apply stimulation amplitudes to corresponding brain regions;
process the acquired signals to generate a second spatial derivative corresponding to the array of sensing electrodes;
find an indication of at least one brain region with atypical neuronal activity; and
responsive to finding the indication, determine a distribution of stimulation amplitudes over an array of the stimulation electrodes based on the second spatial derivative.

33. The non-transitory computer readable storage medium of claim 32, further comprising instructions that cause the processor to apply the spatial distribution of stimulation amplitudes to the array of stimulation electrodes in order to stimulate the at least one region with atypical neuronal activity.

34. The non-transitory computer readable medium of claim 32, wherein the instructions that cause the processor to generate the second spatial derivative include instructions that cause the processor to band pass filter the acquired signals to generate the second spatial derivative.

35. The non-transitory computer readable medium of claim 32, wherein the instructions that cause the processor to generate the second spatial derivative include instructions that cause the processor to extract at least one specific feature from the acquired signals.

36. The non-transitory computer readable medium of claim 35, wherein the instructions that cause the processor to generate the second spatial derivative include instructions that cause the processor to generate the second spatial derivative based on the extracted specific feature.

37. A system for deep brain stimulation, the system comprising:
an implantable probe with an array of sensing electrodes and an array of stimulation electrodes, wherein the array of sensing electrodes and the array stimulation electrodes are arranged on a common surface of the implantable probe, wherein the implantable probe is configured to be implanted into brain tissue, wherein the array of sensing electrodes is configured to acquire signals representing neuronal activity at corresponding positions in a brain, and wherein the array of stimulation electrodes is configured to be implanted into brain tissue and apply stimulation amplitudes to corresponding brain regions; and
a processor, operably coupled to the array of sensing electrodes and the array of stimulation electrodes, configured to:
receive the acquired signals from the array of sensing electrodes,
process the acquired signals to generate a second spatial derivative of the acquired signals received from the sensing electrodes,
find an indication of at least one brain region with atypical neuronal activity,
responsive to finding the indication, determine a spatial distribution of stimulation amplitudes over the array of stimulation electrodes based on the second spatial derivative, and
apply the spatial distribution of stimulation amplitudes to the array of stimulation electrodes.

38. The system of claim 37, wherein the processor is configured to generate the spatial distribution of stimulation amplitudes such that the stimulation current distributed to each of the stimulation electrodes is determined based on values of the second spatial derivative of the acquired signals received from corresponding sensing electrodes.

39. The system of claim 38, wherein the corresponding sensing electrodes are adjacent the respective stimulation electrodes.

40. The system of claim 38, wherein at least some of the corresponding sensing electrodes are the same as and combined with the respective stimulation electrodes.

41. The system of claim 37, wherein the processor is configured to generate the spatial distribution of stimulation amplitudes such that the stimulation current distributed to each of the stimulation electrodes is at a largest level for stimulation electrodes that have corresponding sensing electrodes for which the second spatial derivative of the acquired signals received from the corresponding sensing electrodes has largest values.

42. The system of claim 41, wherein the corresponding sensing electrodes are adjacent the respective stimulation electrodes.

43. The system of claim 41, wherein at least some of the corresponding sensing electrodes are the same as the respective stimulation electrodes.

44. The system of claim 37, wherein the array of sensing electrodes includes a 1-dimensional array of sensing electrodes.

45. The system of claim 44, wherein the second spatial derivative includes a second spatial derivative of the acquired signals received by the 1-dimensional array of sensing electrodes.

46. The system of claim 44, wherein the sensing electrodes of the 1-dimensional array are equally spaced by a 0.5 millimeter distance.

47. The system of claim 44, wherein the 1-dimensional array of sensing electrodes includes 33 sensing electrodes.

48. The system of claim 44, wherein the 1-dimensional array of sensing electrodes comprises a length of 16 millimeters.

49. The system of claim 37, wherein the array of stimulating electrodes includes a 1-dimensional array of stimulating electrodes.

50. The system of claim 49, wherein the spatial distribution of stimulation amplitudes includes a spatial distribution of stimulation amplitudes applied to the 1-dimensional array of stimulating electrodes.

51. The system of claim 49, wherein the stimulating electrodes of the 1-dimensional array are equally spaced by a 0.5 millimeter distance.

52. The system of claim 49, wherein the 1-dimensional array of stimulating electrodes includes 33 sensing electrodes.

53. The system of claim 49, wherein the 1-dimensional array of stimulating electrodes comprises a length of 16 millimeters.

* * * * *